US009752906B2

(12) United States Patent
Suzuki (10) Patent No.: US 9,752,906 B2
(45) Date of Patent: Sep. 5, 2017

(54) FLOW VOLUME DETECTOR

(75) Inventor: Hideyuki Suzuki, Nagoya (JP)

(73) Assignee: AICHI TOKEI DENKI CO., LTD., Nagoya (JP)

(*) Notice: Subject to any disclaimer, the term of this patent is extended or adjusted under 35 U.S.C. 154(b) by 175 days.

(21) Appl. No.: 14/400,730

(22) PCT Filed: May 21, 2012

(86) PCT No.: PCT/JP2012/062912
§ 371 (c)(1),
(2), (4) Date: Nov. 12, 2014

(87) PCT Pub. No.: WO2013/175547
PCT Pub. Date: Nov. 28, 2013

(65) Prior Publication Data
US 2015/0135848 A1    May 21, 2015

(51) Int. Cl.
*G01F 1/58* (2006.01)
*A61M 1/16* (2006.01)
*G01F 15/02* (2006.01)

(52) U.S. Cl.
CPC ............... *G01F 1/58* (2013.01); *A61M 1/16* (2013.01); *A61M 1/1647* (2014.02); *G01F 1/588* (2013.01); *G01F 15/02* (2013.01); *A61M 2205/3317* (2013.01); *A61M 2205/3324* (2013.01); *A61M 2205/3334* (2013.01); *A61M 2205/3368* (2013.01)

(58) Field of Classification Search
CPC ............ G01F 1/588; G01F 15/02; G01F 1/58; A61M 1/1647

USPC ..... 73/204.12, 204.13, 861.11, 1.25, 861.52, 73/861.63, 204.18, 204.19, 204.26
See application file for complete search history.

(56) References Cited

U.S. PATENT DOCUMENTS

| 4,538,925 A * | 9/1985 | Zgonik ................. G01K 17/08 374/15 |
| 4,542,650 A | 9/1985 | Renken et al. |
| 5,736,650 A * | 4/1998 | Hiron et al. ............. G01F 1/44 73/861.04 |
| 7,571,655 B1 * | 8/2009 | Feller ..................... G01F 1/584 73/861.12 |

(Continued)

FOREIGN PATENT DOCUMENTS

| CN | 1730108 A | 2/2006 |
| JP | 60-15629 U | 2/1985 |

(Continued)

OTHER PUBLICATIONS

Machine translation of written specification of WO 2008132956 A1, Date: Nov. 6, 2008, Publisher: European Patent Office via Espacenet, pp. 7.*

(Continued)

*Primary Examiner* — Lisa Caputo
*Assistant Examiner* — Roger Hernandez-Prewitt
(74) *Attorney, Agent, or Firm* — Proskauer Rose LLP (57) ABSTRACT

A base (41) includes a plurality of flow channels (33, 34) and detection sections (531, 541) for detecting the flow volumes of fluids flowing in the flow channels (33, 34). In the base (41), a blocking section (57) for blocking heat conduction between the flow channels (33, 34) is provided between the flow channels (33, 34). The blocking section (57) is configured of groove (58) formed in the base (41).

8 Claims, 8 Drawing Sheets

(56) References Cited

U.S. PATENT DOCUMENTS

| | | | | |
|---|---|---|---|---|
| 7,631,562 B1 * | 12/2009 | Speldrich | ............... | G01F 1/68 |
| | | | | 73/861.52 |
| 2006/0030917 A1 | 2/2006 | Eccleston et al. | | |
| 2011/0247411 A1 * | 10/2011 | Speldrich | ............ | B29C 45/0025 |
| | | | | 73/273 |

FOREIGN PATENT DOCUMENTS

| | | |
|---|---|---|
| JP | 60-50419 A | 3/1985 |
| JP | 05-87603 A | 4/1993 |
| JP | 2004-93392 A | 3/2004 |
| JP | 2011-191069 A | 9/2011 |
| WO | 2006027565 A1 | 3/2006 |
| WO | 2008/132956 A1 | 11/2008 |

OTHER PUBLICATIONS

Authors: M Dijkstra, M J de Boer, J W Berenschot, T S J Lammerink, R J Wiegerink and M Elwenspoek, Title: A versatile surface channel concept for microfluidic applications, Publication: Journal of Micromechanics and Microengineering, Date: Sep. 5, 2007, pp. 1971-1977.*

International Search Report for PCT/JP2012/062912, dated Aug. 7, 2012 (2 pages).

International Preliminary Report on Patentability (Englsh translation), International Application No. PCT/JP2012/062912, issued Nov. 25, 2014, 6 pages.

"First Office Action," Issued by the State Intellectual Property Office of the People's Republic of China, Issued in Chinese Application No. 201280073265.3, dated Jul. 5, 2016, 14 pages.

* cited by examiner

FLOW VOLUME DETECTOR

FIELD OF THE INVENTION

The present invention relates to a flow volume detector incorporated into a medical artificial dialysis apparatus to detect the flow volume of a dialysate.

BACKGROUND OF THE INVENTION

A flow volume detector of this type is disclosed in Patent Document 1. The flow volume detector disclosed in this document comprises a synthetic resin base which is attached to/detached from a flow volume measuring device. A pair of flow channels, in which a dialysate flows, is formed in the base. The base is provided with a detection terminal and an earth terminal in order to detect the flow volumes of the dialysates flowing in the respective flow channels.

One of the pair of flow channels is connected to an inflow route for conducting a dialysate into a dialyzer of an artificial dialysis apparatus in the state where the flow volume detector is attached to the flow volume measuring device. The other flow channel is connected to a return route for returning the dialysate from the dialyzer. The respective flow channels are arranged between a pair of magnetic poles of a magnetic circuit including an electromagnetic coil in the flow volume measuring device.

When the artificial dialysis apparatus is operated in this state, blood containing waste matter derived from a patient is introduced into the dialyzer and filtered. After transfer of the waste matter and moisture separated by filtration into the dialysate, clean blood after dialysis is returned to the patient again. At this time, electromotive forces, which are proportional to the flow rates of the dialysates flowing in the respective flow channels, are developed. The electromotive forces are detected by the respective detection terminals, and the flow volumes of the dialysates flowing in the respective flow channels are measured based on the flow rates of the dialysates and the sectional areas of the flow channels. Then, the amount of the waste matter separated from blood is calculated based on the difference between the flow volumes of the dialysates flowing in the respective flow channels.

According to the flow volume detector disclosed in this document, the pair of flow channels is formed adjacent to each other. Therefore, the base may be deformed if the temperature of a fluid flowing in one of the pair of flow channels becomes high. This is likely to cause a change in sectional area of the other of the pair of flow channels, resulting in the occurrence of an error in the measurement of the flow volume of the dialysate.

PRIOR ART DOCUMENTS

Patent Documents

Patent Document 1: Japanese Laid-Open Patent Publication No. 2011-191069

SUMMARY OF THE INVENTION

An object of the present invention is to prevent the temperature of a fluid flowing in one flow channel from affecting the other flow channel, i.e., to provide a flow volume detector which can appropriately hold the sectional areas of the respective flow channels and can also accurately measure the flow volumes of fluids flowing in the respective channels.

In order to attain the above object, according to a first aspect of the present invention, there is provided a flow volume detector comprising a base, a plurality of flow channels formed in the base and detecting sections which detect the flow volumes of fluids flowing in the plurality of flow channels. A blocking section for blocking heat conduction between the flow channels is provided between the plurality of flow channels.

According to this configuration, the temperature of a fluid flowing in one flow channel may change in some cases. Even in such a case, heat conduction from one flow channel to the other flow channel is blocked by the blocking section provided between the flow channels. Thus, the temperature of the fluid flowing in the one flow channel does not affect the other flow channel. This makes it possible to suitably hold the sectional areas of the respective flow channels and to accurately measure the flow volumes of the fluids flowing in the flow channels.

In the flow volume detector, the blocking section is preferably configured of a groove formed in the base.

In the flow volume detector, the groove preferably penetrates from the front face of the base to its back face.

In the flow volume detector, the detecting sections are preferably arranged in the center part in the longitudinal direction of the groove.

In the flow volume detector, preferably, orifice-shaped measurement flow generating sections are formed in the flow channels, and the detecting sections are arranged in the measurement flow generating sections.

In the flow volume detector, preferably, in the measurement flow generating sections, inclined parts are formed in both end parts in a direction in which fluids flow, and the inclined parts are formed such that the flow channels become narrower as the flow channels go toward the measurement flow generating sections.

In the flow volume detector, preferably, the detecting sections have terminals arranged in end parts on both sides in the width direction of the measurement flow generating sections, and the terminals preferably detect electromotive forces developed by flowing fluids.

In the flow volume detector, preferably, the plurality of flow channels are configured by a pair of flow channels, and the pair of flow channels are respectively arranged in the same plane on both sides of the groove and sandwiching the groove.

According to the present invention, the temperature of a fluid flowing in one flow channel is prevented from affecting the other channel, thereby making it possible to suitably hold the sectional areas of the respective flow channels and to accurately measure the flow volumes of the fluids flowing in the flow channels.

DETAILED DESCRIPTION OF THE PREFERRED EMBODIMENTS

First Embodiment

Hereinafter, a first embodiment of a flow volume detector according to the present invention will be explained in accordance with FIGS. 1 to 9.

Figure 1:
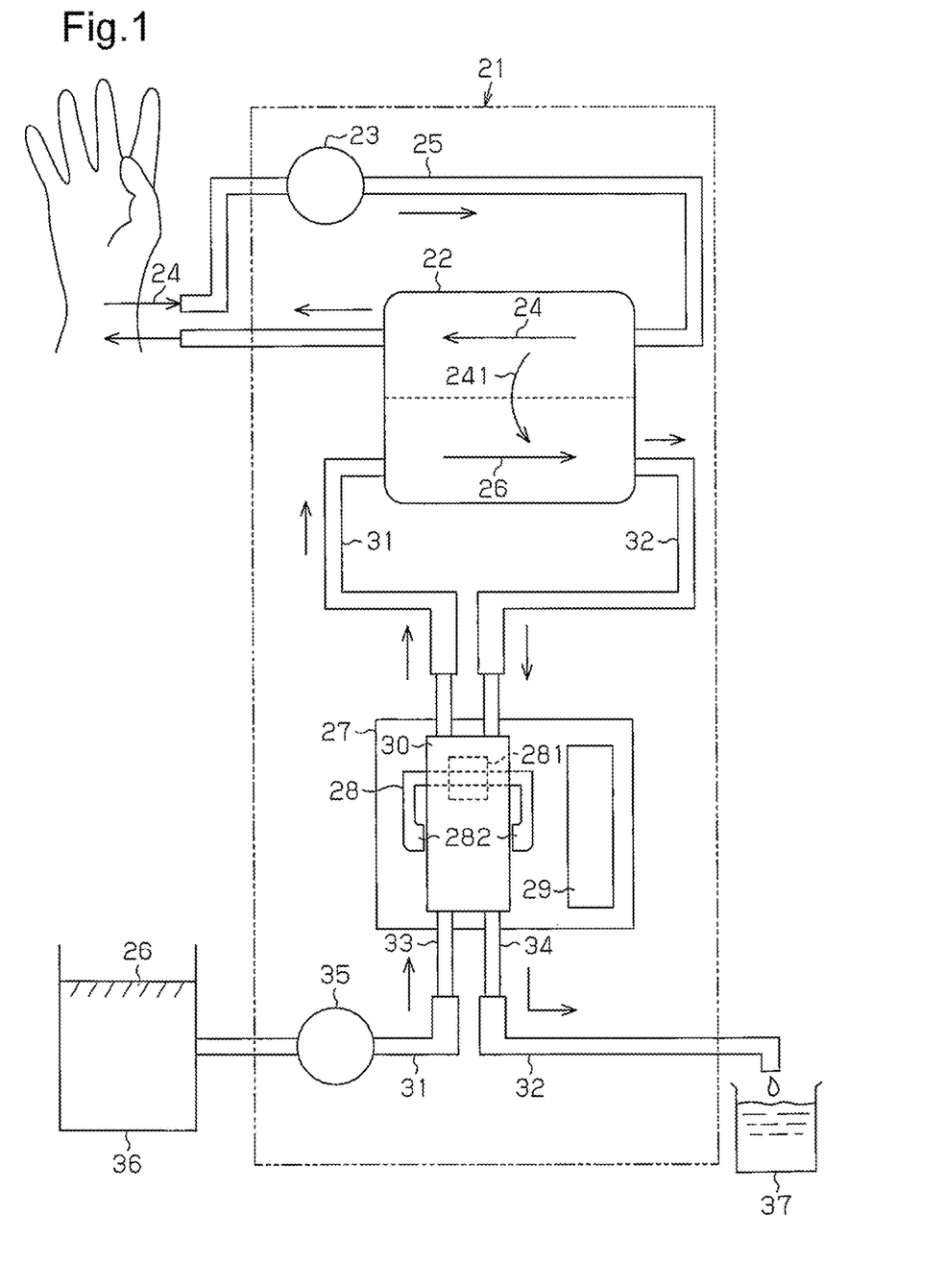
FIG. 1 is a schematic block diagram showing a medical artificial dialysis apparatus into which a flow volume detector according to a first embodiment of the present invention is incorporated.

As shown in FIG. 1, an artificial dialysis apparatus 21 comprises a dialyzer 22. Upon operation of a pump 23, blood 24 containing waste matter 241 derived from the body of a patient is introduced into the dialyzer 22 via a blood circulation route 25. When the blood 24 is filtered by the dialyzer 22, the waste matter 241 in the blood is separated and taken in a dialysate 26 as a fluid. The clean blood 24 after filtration is returned to the patient's body.

The artificial dialysis apparatus 21 further comprises a flow volume measuring device 27. The flow volume measuring device 27 is provided with a magnetic circuit 28 comprising an electromagnetic coil 281 and a pair of magnetic poles 282 and a signal processing circuit 29 for processing a measurement signal. An alternating current is supplied to the electromagnetic coil 281.

A disposable type flow volume detector 30 is attached to the flow volume measuring device 27 in order to measure the flow volume of a dialysate 26. The flow volume detector 30 is configured to be attachable to/detachable from the flow volume measuring device 27. The flow volume detector 30 is provided with a pair of flow channels 33, 34. The flow channels 33, 34 are connected to an inflow route 31 and a return route 32, respectively, for the dialysate 26 with respect to the dialyzer 22.

Both the flow channels 33, 34 are arranged between both the magnetic poles 282 of the magnetic circuit 28 in the state where the flow volume detector 30 is attached to the flow volume measuring device 27. Upon operation of the pump 35 in this state, the dialysate 26 is allowed to flow into the dialyzer 22 via the inflow route 31 and flow channel 33 from a supply tank 36. The dialysate 26 containing the waste matter 241 separated by the dialyzer 22 is returned to a drain tank 37 via the return route 32 and flow channel 34. At this time, the flow volumes of the dialysates 26 flowing in the respective flow channels 33, 34 are respectively measured by the flow volume detector 30.

Figure 2:
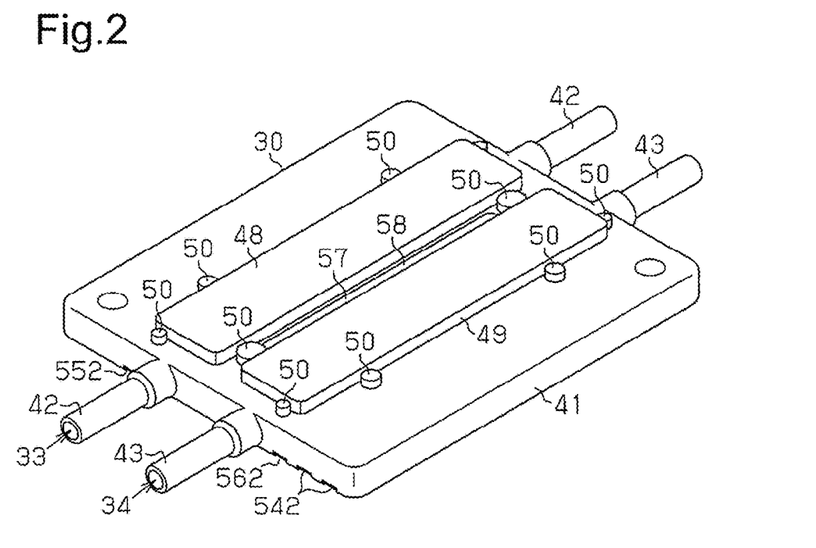
FIG. 2 is a perspective view of the flow volume detector.
Figure 3:
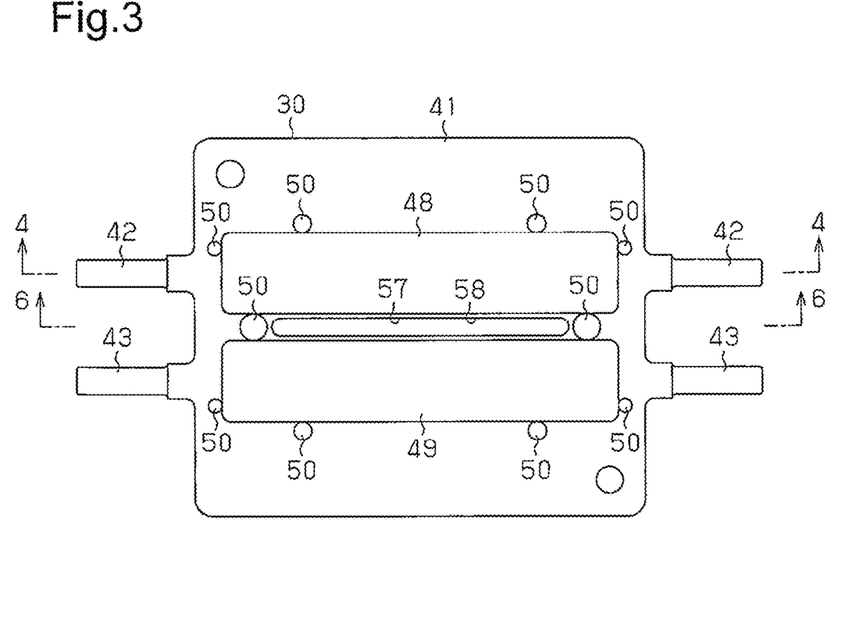
FIG. 3 is a plan view of the flow volume detector.
Figure 4:
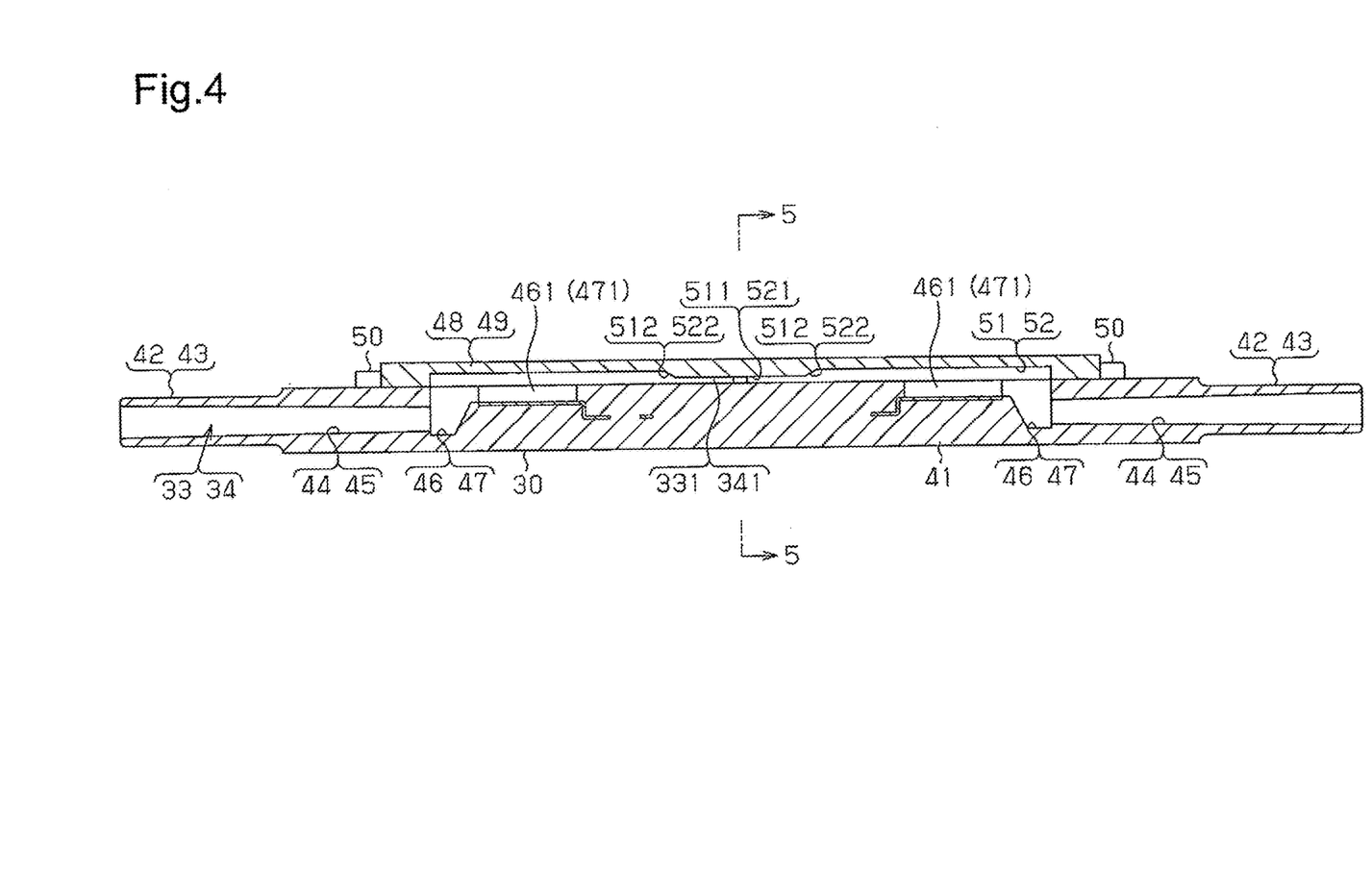
FIG. 4 is a cross sectional view along a 4-4 line in FIG. 3.

As shown in FIGS. 2 and 3, the flow volume detector 30 comprises a base 41 made of a transparent synthetic resin such as a polypropylene resin. The base 41 is formed into a rectangular plate form. From both end faces of the base 41, a pair of connection pipes 42, 43 is respectively protruded. The respective connection pipes 42, 43 are connected to the middle of the inflow route 31 and return route 32. As shown in FIG. 4, concave parts 46, 47, which are in communication with passages 44, 45 within the respective connection pipes 42, 43, are formed in both end parts of the base 41. The passages 44, 45 are connected to the concave parts 46, 47, respectively, in positions slightly higher than the bottom faces of the concave parts 46, 47. Groove parts 461, 471 are formed at sites near to the center of the base 41 in the concave parts 46, 47. The groove parts 461, 471 are shallower than the concave parts 46, 47 and are arranged in positions higher than the passages 44, 45.

Figure 6:
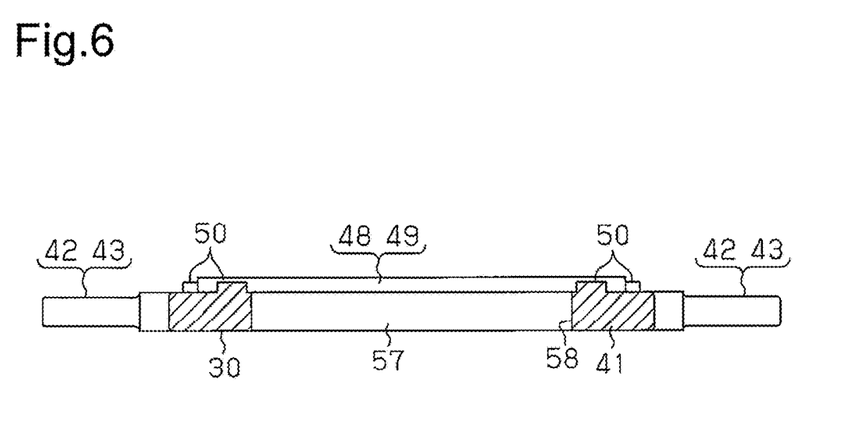
FIG. 6 is a cross sectional view along a 6-6 line in FIG. 3.

As shown in FIGS. 2 and 6, a part of lid plates 48, 49 are adhered or welded onto the upper face of the base 41. The lid plates 48, 49 are formed of a transparent synthetic resin such as a polypropylene resin. The respective lid plates 48, 49 are positioned in predetermined positions on the base 41 by a plurality of positioning pins 50. As shown in FIG. 4, measurement groove parts 51, 52, which are in communication with the concave parts 46, 47 and groove parts 461, 471, are formed on the back face of the respective lid plates 48, 49. Convex parts 511, 521 are formed in the center parts in the longitudinal direction of the respective measurement groove parts 51, 52. Inclined parts 512, 522 are formed in both end parts of the convex parts 511, 521.

Figure 5:
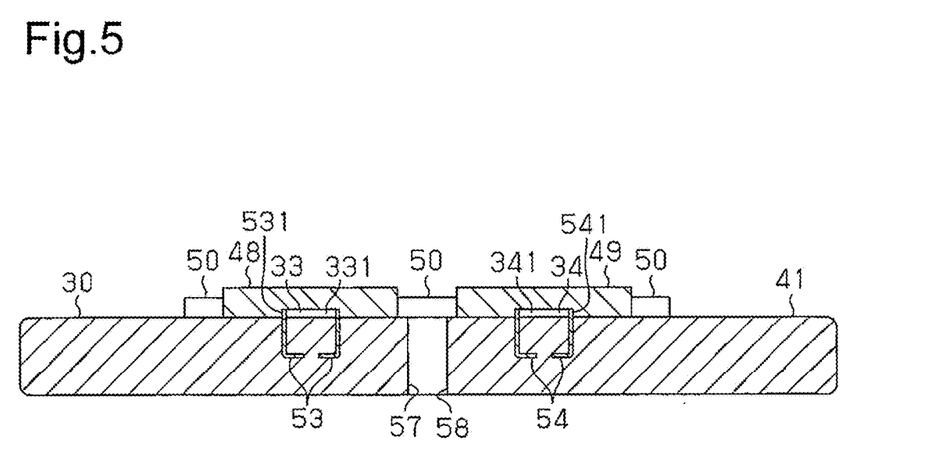
FIG. 5 is a cross sectional view along a 5-5 line in FIG. 4.

As shown in FIGS. 4 and 5, the flow channel 33 is configured of the passage 44 of the connection pipe 42, the concave part 46, the groove part 461 and the measurement groove part 51 of the lid plate 48 in a state where the lid plates 48, 49 are fixed on the base 41. Also, the flow channel 34 is configured of the passage 45 of the connection pipe 43, the concave part 47, the groove part 471 and the measurement groove part 52 of the lid plate 49. Orifice-shaped measurement flow generating sections 331, 341 are formed between the convex parts 511, 521 of the respective lid plates 48, 49 and the upper face of the base 41. The respective measurement flow generating sections 331, 341 have passage sectional areas suitable to generate the measurement flows of the dialysates 26 in the respective flow channels 33, 34.

Figure 7:
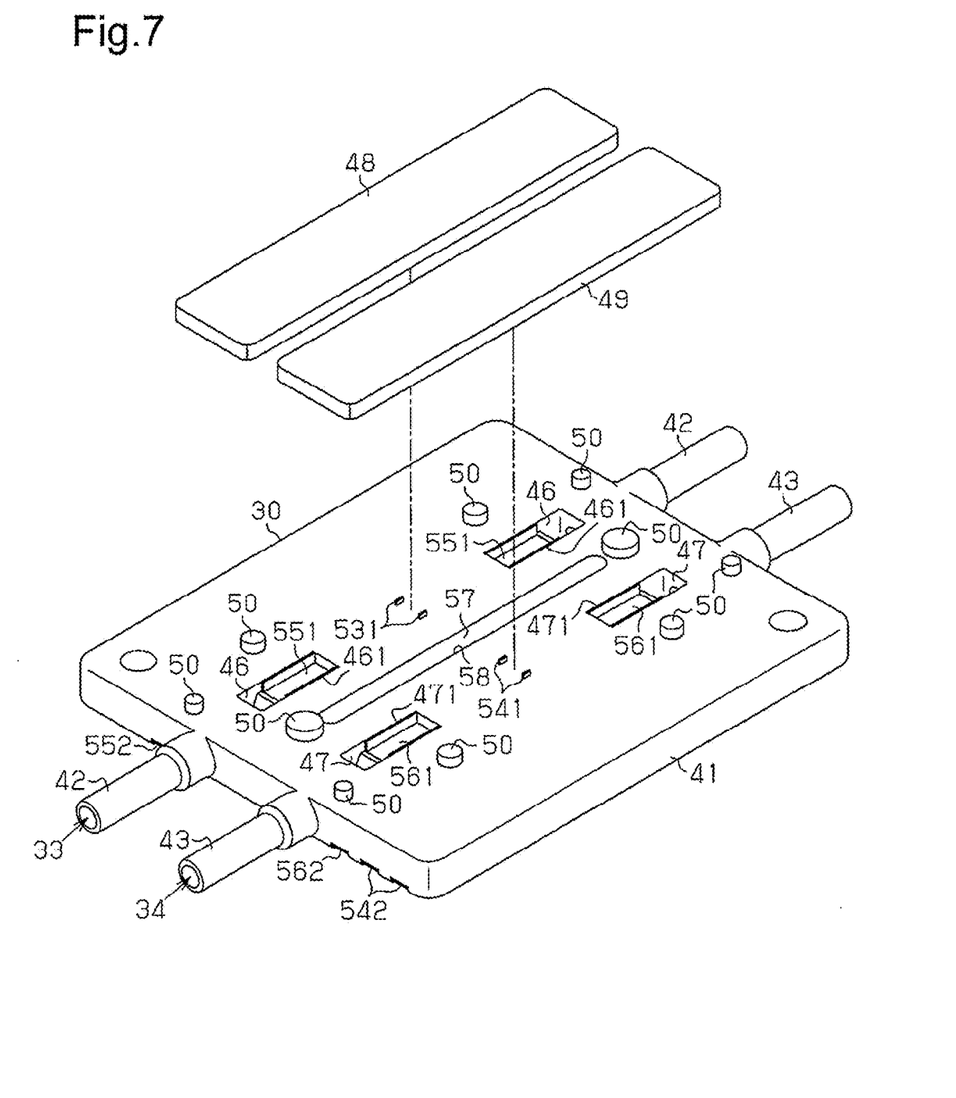
FIG. 7 is a perspective view showing the state where the flow volume detector is decomposed into a base and a lid plate.
Figure 8:
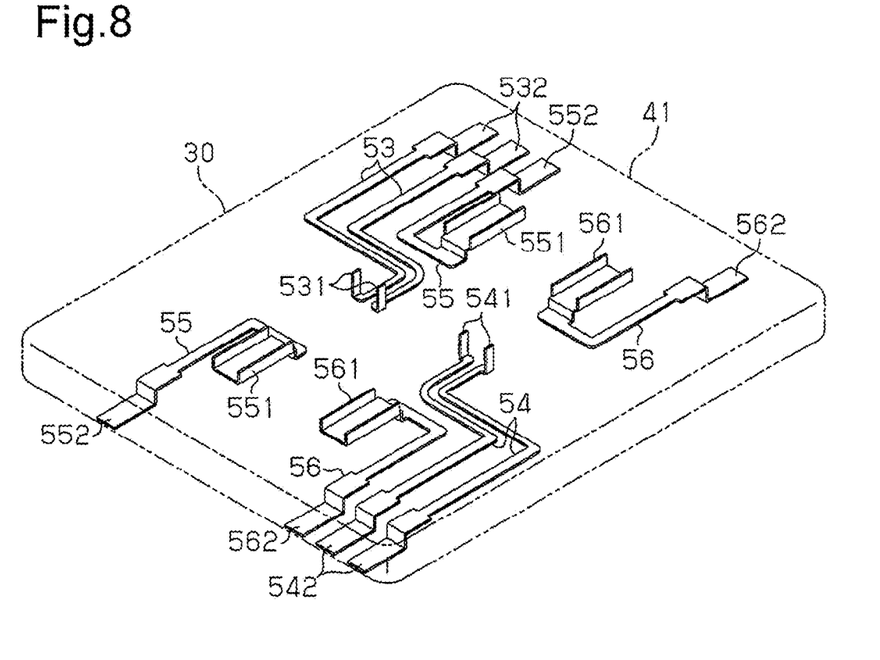
FIG. 8 is a perspective view showing a detection terminal and an earth terminal of the flow volume detector.
Figure 9:
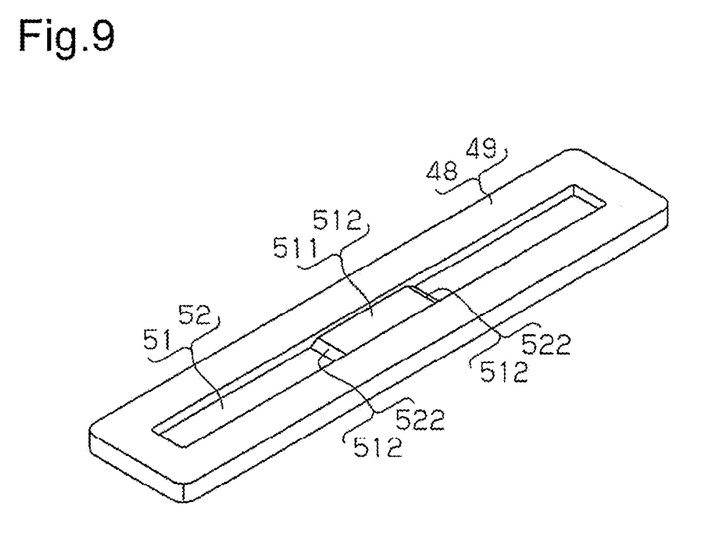
FIG. 9 is a perspective view of the lid plate of the flow volume detector when viewed from the rear side.

As shown in FIGS. 5, 7, and 8, a pair of detection bus bars 53 and a pair of detection bus bars 54 are embedded within the base 41. A detection terminal 531 as a detecting section, which is exposed within the measurement flow generating section 331, is formed in the first end of the respective detection bus bars 53. A detection terminal 541 as a detecting section, which is exposed within the measurement flow generating section 341, is formed in the first end of the respective detection bus bars 54. The detection terminals 531, 541 are arranged opposite to each other in end parts in the width direction of the measurement flow generating sections 331, 341. As shown in FIGS. 2 and 8, connection terminals 532, which are exposed to the end face of the base 41, are respectively formed in the second end parts of the respective detection bus bars 53. Connection terminals 542, which are exposed to the end face of the base 41, are respectively formed in the second end parts of the respective detection bus bars 54. The connection terminals 532, 542 are connected to a signal processing circuit 29 of the flow volume measuring device 27.

Within the base 41, an earth bus bar 55 and an earth bus bar 56 are embedded. Earth terminals 551, 561, which are exposed within the groove parts 461, 471, are respectively formed in the first end parts of the respective earth bus bars 55, 56. Connection terminals 552, 562, which are exposed to the end face of the base 41, are respectively formed in the second end parts of the respective earth bus bars 55, 56. The connection terminals 552, 562 are connected to the signal processing circuit 29.

As shown in FIGS. 3 and 6, a blocking section 57 is provided in the center between both the flow channels 33, 34 in the base 41. The blocking section 57 blocks heat conduction from one of the pair of flow channels 33, 34 through the base 41 to the other flow channel. In the first embodiment, the blocking section 57 extends along the flow channels 33, 34 between both the flow channels 33, 34. Namely, the blocking section 57 is configured of a through groove 58 penetrating from the front face of the base 41 toward its back face. Both the flow channels 33, 34 are arranged in the same plane on both sides sandwiching the through groove 58. The detection terminals 531, 541 are arranged in the center part in the longitudinal direction of the through groove 58.

Next, the action of the artificial dialysis apparatus including the flow volume detector 30 described above will be explained.

As shown in FIG. 1, the flow volume detector 30 is attached to the flow volume measuring device 27 when the artificial dialysis apparatus 21 is used. In this state, the flow channel 33 is connected to the middle of the inflow route 31, and the flow channel 34 is connected to the middle of the return route 32. In this state, the measurement flow generating sections 331, 341 of the respective flow channels 33, 34 shown in FIG. 4 are arranged between the pair of magnetic poles 282 of the magnetic circuit 28.

Upon operation of the artificial dialysis apparatus 21 in this state, the blood 24 derived from a patient is introduced into the dialyzer 22 via the blood circulation route 25 by actuation of the pump 23. Also, the dialysate 26 within the supply tank 36 is allowed to flow into the dialyzer 22 via the inflow route 31 and flow channel 33 by actuation of the pump 35. Therefore, the blood 24 is filtered with the dialyzer 22, and, simultaneously, the waste matter 241 in the blood 24 is separated and transferred into the dialysate 26. The cleaned blood 24 is returned to the patient via the blood circulation route 25. Also, the dialysate 26 containing the waste matter 241 is recovered to a drain tank 37 via the return route 32 and flow channel 34.

At this time, an alternating field is generated by an alternating current in the magnetic circuit 28. The magnetic flux penetrates the measurement flow generating sections 331, 341 of the respective flow channels 33, 34. Therefore, electromotive forces corresponding to the flow rates of the dialysates 26 flowing in the measurement flow generating sections 331, 341 are developed. The electromotive forces are output as detection signals from the detection terminals 531, 541 of the respective detection bus bars 53, 54 to the signal processing circuit 29. The detection signals are output at a level set according to the earth potential from the earth bus bars 55, 56. From the detection signals, the flow volumes per unit time of the dialysates 26 flowing in the respective flow channels 33, 34 are respectively measured from the detection signal based on the flow rates of the dialysates 26 and the sectional areas of the measurement flow generating sections 331, 341. The amount of the waste matter 241 separated from the blood 24 is calculated based on the difference between the flow volumes of the dialysates 26 flowing in both the flow channels 33, 34.

In the measurement of the flow volumes of the dialysates 26, when the temperature of the dialysate 26 flowing in one of the flow channels 33, 34 changes, the base 41 made of a synthetic resin and the lid plate 48 may expand or contract. This is likely to cause a change in sectional area of the measurement flow generating sections 331, 341 in the other of the flow channels 34, 33, resulting in the occurrence of an error in the measurement of the flow volume. In this regard, according to the first embodiment, the through groove 58 is formed as the blocking section 57 for substantially blocking heat conduction between both the flow channels 33, 34 on the base 41. Therefore, the temperature of the dialysate 26 flowing in one of the flow channels 33, 34, even if changed, hardly affects the other flow channel by virtue of the through groove 58.

Accordingly, the first embodiment can provide the following advantageous effects.

(1) The blocking section 57 for blocking heat conduction between the flow channels 33, 34 is provided between the flow channels 33, 34. Therefore, even if the temperature of the dialysate 26 flowing in one of the flow channels 33, 34 changes, heat conduction from the one flow channel to the other flow channel is blocked by virtue of the blocking section 57. Accordingly, the temperature of the dialysate 26 flowing in one of the flow channels 33, 34 hardly affects the other flow channel. Thus, it is possible to appropriately hold the sectional areas of the respective flow channels 33, 34 and to accurately measure the flow volumes of the dialysates 26 flowing in the flow channels 33, 34.

(2) The blocking section 57 is configured of the through groove 58 formed in the base 41. This configuration ensures a simple structure of the blocking section 57 and effective blocking of heat conduction between the flow channels 33, 34.

(3) The through groove 58 penetrates from the front face of the base 41 toward its back face. Therefore, it is also possible to block heat conduction between the flow channels 33, 34 at a high level and to maintain a high blocking rate.

(4) The inclined parts 512, 522 are formed in both end parts of the convex parts 511, 521 forming the measurement flow generating sections 331, 341. This configuration makes the flow of the dialysates 26 difficult to be disturbed even if the sectional areas of the flow channels in the concave parts 511, 521 and on both sides of the convex parts 511, 521 are different. Therefore, the flow volumes of the dialysates 26 can be accurately detected.

(5) The concave parts 46, 47 and groove parts 461, 471 are formed between the passages 44, 45 of the connection pipes 42, 43 and the measurement groove parts 51, 52 of the lid plates 48, 49. According to this configuration, the dialysates 26 are temporarily stored in the concave parts 46, 47 and the groove parts 461, 471. This makes the flow of the dialysates 26 difficult to disturb. Therefore, the flow volumes of the dialysates 26 can be accurately detected.

(6) The detection terminals 531, 541 of the detection bus bars 53, 54 are arranged in the center in the longitudinal direction of the through groove 58. In this case, the detection terminals 531, 541 are arranged in positions which are difficult to be affected by heat from a flow channel different from the flow channel in which the detection terminals are arranged. This makes it possible to accurately detect the flow volumes of the dialysates 26.

(7) The flow channels 33, 34 are arranged in the same plane on both sides sandwiching the through groove 58. Therefore, it is possible to form the flow volume detector 30 in a flat and compact shape.

Second Embodiment

Next, a second embodiment of the flow volume detector 30 according to the present invention will be explained with reference to FIG. 10. The second and subsequent embodiments and altered examples will be explained mainly in terms of their differences from the first embodiment.

Figure 10:
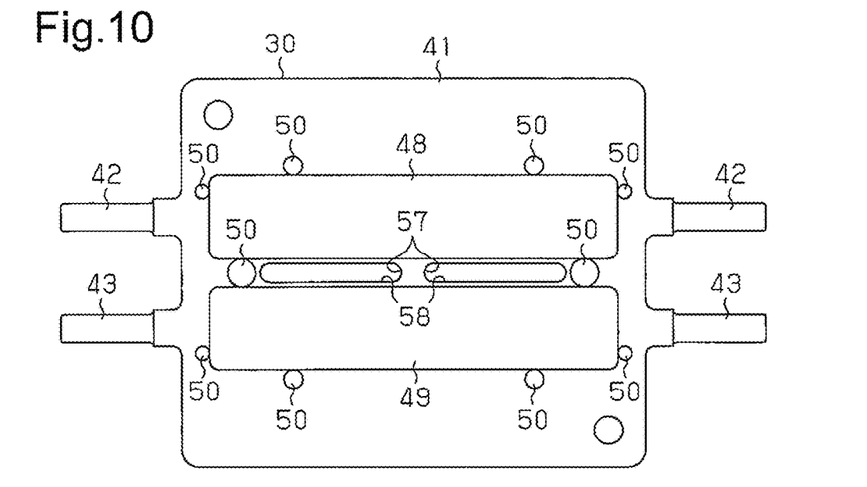
FIG. 10 is a plan view showing a flow volume detector according to a second embodiment of the present invention.

A through groove 58 as a blocking section 57 is divided into two parts in the longitudinal direction, as shown in FIG. 10.

Thus, the second embodiment can provide the following advantageous effect.

(8) Since the length of one through groove 58 is made shorter, it is possible to suppress the deformation of a portion between the measurement groove parts 51, 52 of the base 41. Accordingly, the reinforcing action of the base 41 can be obtained.

Third Embodiment

Next, a third embodiment of the flow volume detector 30 according to the present invention will be explained with reference to FIG. 11.

Figure 11:
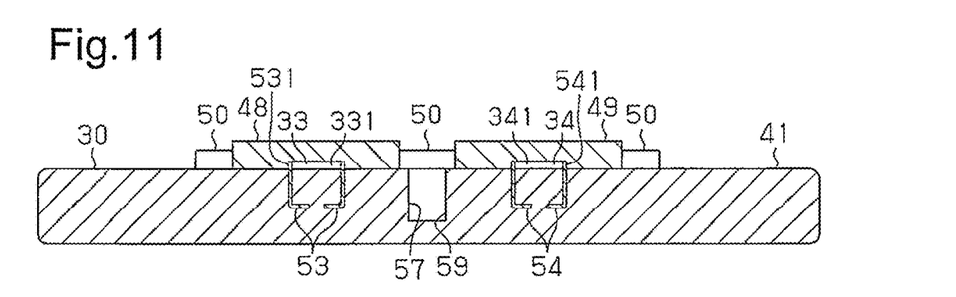
FIG. 11 is a cross sectional view showing a flow volume detector according to a third embodiment of the present invention.

As shown in FIG. 11, a blocking section 57 is configured of a concave groove 59 formed in the upper face of the base 41. The concave groove 59 has a bottom wall. The concave groove 59 are provided between both flow channels 33, 34 and extend along the flow channels 33, 34.

Thus, the third embodiment can provide the following advantageous effect.

(9) Since the concave groove 59 has a bottom wall, it is possible to suppress the deformation of the base 41 as a whole and to obtain the reinforcing effect of the base 41.

Fourth Embodiment

Next, a fourth embodiment of the flow volume detector 30 according to the present invention will be explained with reference to FIG. 13.

Figure 12:
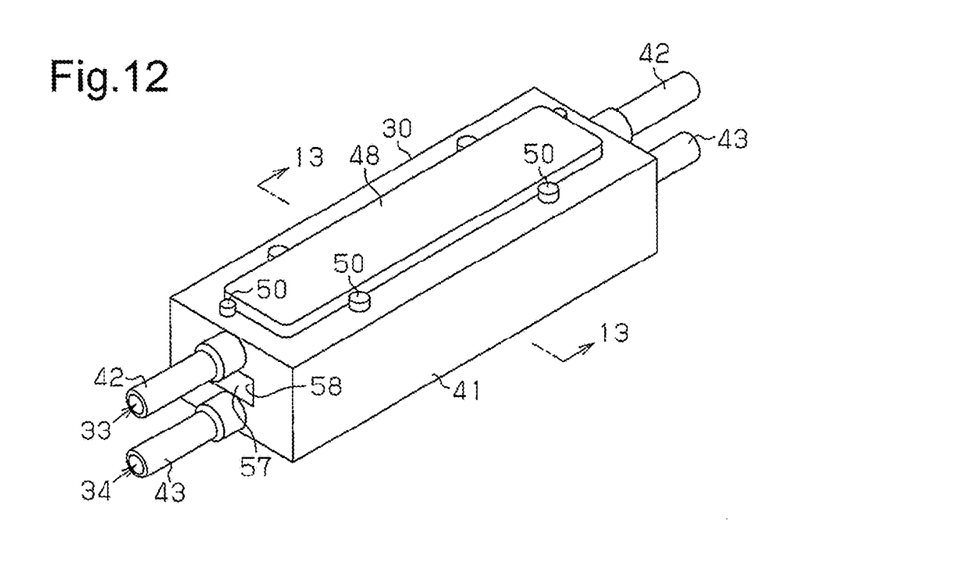
FIG. 12 is a perspective view showing a flow volume detector according to a fourth embodiment of the present invention.
Figure 13:
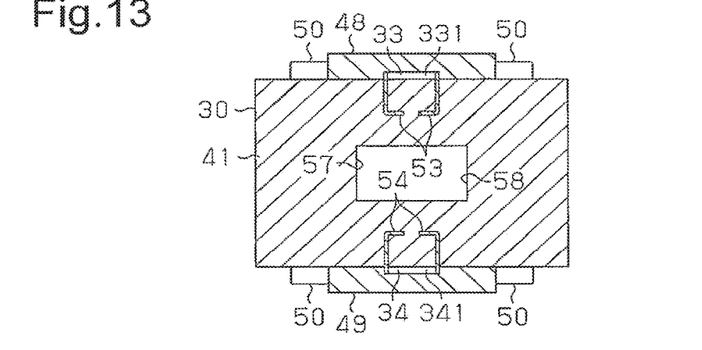
FIG. 13 is a cross sectional view along a 13-13 line in FIG. 12.

As shown in FIGS. 12 and 13, a pair of flow channels 33, 34 is formed such that they are spaced apart in the thickness direction of a base 41 and overlap each other. A through groove 58 as a blocking section 57 is provided between the flow channels 33, 34. The through groove 58 penetrates from one of both ends of the base 41 to the other.

Thus, the fourth embodiment can provide the following advantageous effect.

(10) The flow channels 33, 34 are formed on both sides of the through groove 58 and sandwiching the through groove 58 such that they overlap each other in the thickness direction of the base 41. This configuration makes it possible to narrow the width of the base 41 and downsize the entire base 41. Since it is also possible to flow a cooling medium in the through groove 58, the temperature of the flow volume detector 30 can be managed more easily.

Fifth Embodiment

Next, a fifth embodiment of the flow volume detector 30 according to the present invention will be explained with reference to FIG. 14.

Figure 14:
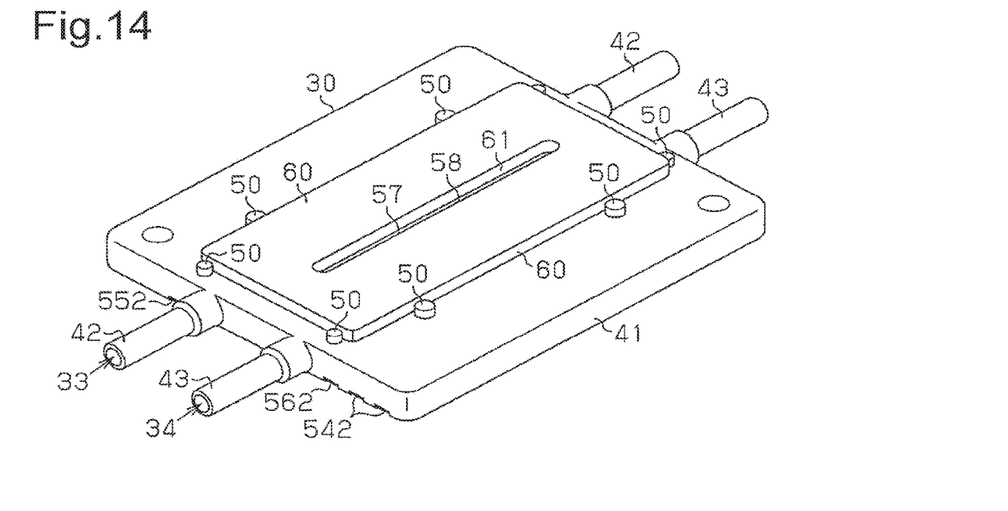
FIG. 14 is a perspective view showing a flow volume detector according to a fifth embodiment of the present invention.

As shown in FIG. 14, one lid plate 60 is employed in place of the pair of lid plates 48, 49 in the respective embodiments described above. A through groove 61 as a blocking section which penetrates from the front face of the lid plate 60 toward its back face is formed in the center part of the lid plate 60. The through groove 61 is formed in a position corresponding to the through groove 58 of the base 41. The through groove 61 has almost the same width and length as those of the through groove 58.

Thus, the fifth embodiment can provide the following advantageous effect.

(11) Since only one lid plate 60 is formed, it is possible to reduce the number of parts to simplify the configuration of the flow volume detector.

Sixth Embodiment

Next, a sixth embodiment of the flow volume detector 30 according to the present invention will be explained with reference to FIG. 15.

Figure 15:
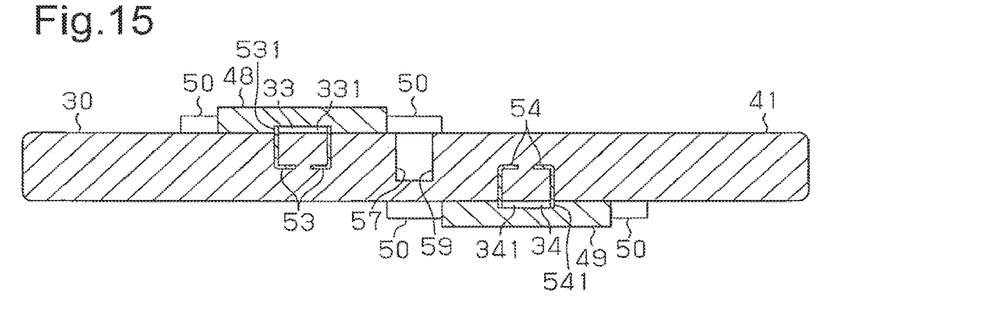
FIG. 15 is a cross sectional view showing a flow volume detector according to a sixth embodiment of the present invention.

As shown in FIG. 15, one of the pair of lid plates 48, 49 is attached to a surface of a base 41 opposite to another surface thereof to which the other lid plate is attached. Therefore, also for a pair of flow channels 33, 34 and detection bus bars 53, 54, one of the flow channels or detection bus bars is provided on a surface of the base 41 opposite to another surface thereof on which the other flow channel or detection bus bar is provided.

Thus, the sixth embodiment can provide the following advantageous effect.

(12) One of the pair of flow channels 33, 34 is provided on a surface of the base 41 opposite to another surface thereof on which the other flow channel is provided. According to this configuration, it is possible to further suppress the temperature of the fluid flowing in one of the pair of flow channels 33, 34 from affecting the other flow channel because of a long distance between the flow channels 33, 34.

In the meantime, the above-described embodiments may be changed as follows.

A heat insulating material such as expanded polystyrene may be packed within the through groove 58 or concave groove 59. That is, the blocking section 57 may be configured of the through groove 58 or concave groove 59 and the heat insulating material.

A plurality of small holes may be linearly and continuously formed to configure the blocking section 57.

The flow volume detector according to the present invention may be used in fields other than artificial dialysis.

The invention claimed is:

1. A flow volume detector which measures the flow volume of a dialysate in an artificial dialysis apparatus, the flow volume detector comprising:
    a base,
    a plurality of flow channels formed in the base;
    a lid plate fixed to an upper face of the base; and
    detecting sections arranged in the flow channels for detecting flow volumes of fluids flowing in the plurality of flow channels,
    wherein a blocking section for blocking heat conduction between the plurality of flow channels is provided between the plurality of flow channels,
    the blocking section is configured of a space including at least a groove formed through the base, the groove penetrates from a front face of the base toward a back face of the base.

2. The flow volume detector according to claim 1, wherein the blocking section is configured of a first groove formed through the base and a second groove formed in a position corresponding to the first groove in the lid plate.

3. The flow volume detector according to claim 1, wherein the detecting sections are arranged in a center part in a longitudinal direction of the groove.

4. The flow volume detector according to claim 1, wherein orifice-shaped measurement flow generating sections are formed in the flow channels, and the detecting sections are arranged in the measurement flow generating sections.

5. The flow volume detector according to claim 4, wherein, in the measurement flow generating sections, inclined parts are formed in both end parts in a direction in which fluids flow, and the inclined parts are formed such that the flow channels become narrower as the flow channels go toward the measurement flow generating sections.

6. The flow volume detector according to claim 4, wherein the detecting sections have terminals arranged in end parts on both sides in a width direction of the measurement flow generating sections, and the terminals detect electromotive forces developed by flowing fluids.

7. The flow volume detector according to claim 1, wherein the plurality of flow channels are configured of a pair of flow channels, and the pair of flow channels are respectively arranged in the same plane on both sides of the groove and sandwiching the groove.

8. A flow volume detector which measures the flow volume of a dialysate in an artificial dialysis apparatus, the flow volume detector comprising:
   a base,
   a plurality of flow channels formed in the base;
   a lid plate fixed to an upper face of the base; and
   detecting sections arranged in the flow channels for detecting flow volumes of fluids flowing in the plurality of flow channels,
   wherein a blocking section for blocking heat conduction between the plurality of flow channels is provided between the plurality of flow channels,
   the blocking section is configured of a space including at least a groove formed in the base, the groove penetrates from a front face of the base toward a back face of the base, and
   wherein the flow channels comprise passages of connection pipes protruding from both end faces of the base, concave parts which are formed in both end parts of the base and are in communication with the passages of the connection pipes, groove parts formed at locations near to the center of the base in the concave parts, and measurement flow generating sections formed in an upper face of the base, wherein the groove parts are shallower than the concave parts and are arranged in positions higher than the passages, and the measurement flow generating sections are arranged in positions higher than the groove parts.

* * * * *